United States Patent [19]

Gibney

[11] Patent Number: 4,919,661

[45] Date of Patent: Apr. 24, 1990

[54] AUTOGENEOUS PUMPING CHAMBER AND PROCEDURES THEREFOR

[76] Inventor: John Gibney, 6236 E. Montecito, Scottsdale, Ariz. 85251

[21] Appl. No.: 71,422

[22] Filed: Jul. 9, 1987

[51] Int. Cl.$^5$ .............................................. A61F 2/22
[52] U.S. Cl. ....................................................... 623/3
[58] Field of Search ........................... 623/3; 128/1 D

[56] References Cited

U.S. PATENT DOCUMENTS

| | | | |
|---|---|---|---|
| 4,652,265 | 3/1987 | McDougall | 623/3 |
| 4,666,443 | 5/1987 | Portner | 623/3 |
| 4,759,760 | 7/1988 | Snapp | 623/3 |
| 4,791,911 | 12/1988 | Magouern | 623/3 |
| 4,813,952 | 3/1989 | Hhalafalla | 623/3 |

OTHER PUBLICATIONS

*Biomechanical Cardiac Assist Cardiomyoplasty and Muscle Powered Devices,* Chapters 11 and 12, Edited by R. C. J. Chiu, 1986.
"Synchronously Stimulated Skeletal Muscle Graft for Myocardial Repair", Dewar et al, *Journal of Thoracic and Cardiovascular Surgery,* vol. 87, No. 3, pp. 325–331, Mar. 1984.
"Cardiac Assist and Myocardial Repair with Synchronously Stimulated Skeletal Muscle", Drinhunter et al, pp. 271–273, Amer. Coll. of Surgeons Surgical Forum, vol. 31, 1980.

*Primary Examiner*—Richard J. Apley
*Assistant Examiner*—James Prizant
*Attorney, Agent, or Firm*—Richard R. Mybeck

[57] ABSTRACT

Means and methods of creating an autogeneous pumping chamber for ventricular replacement or ventricular assist while avoiding heart transplantation. A chamber is created by wrapping a major muscular mass around a silastic-type pouch which is thereafter filled with isotonic saline. The muscular mass is then allowed to grow together over time to create an autogeneous fluid-tight pumping chamber, the pouch is then drained and removed, and the autogeneous chamber is relocated to its needed location, and thereafter grafted into operative relationship within the cardiovascular system.

10 Claims, 2 Drawing Sheets

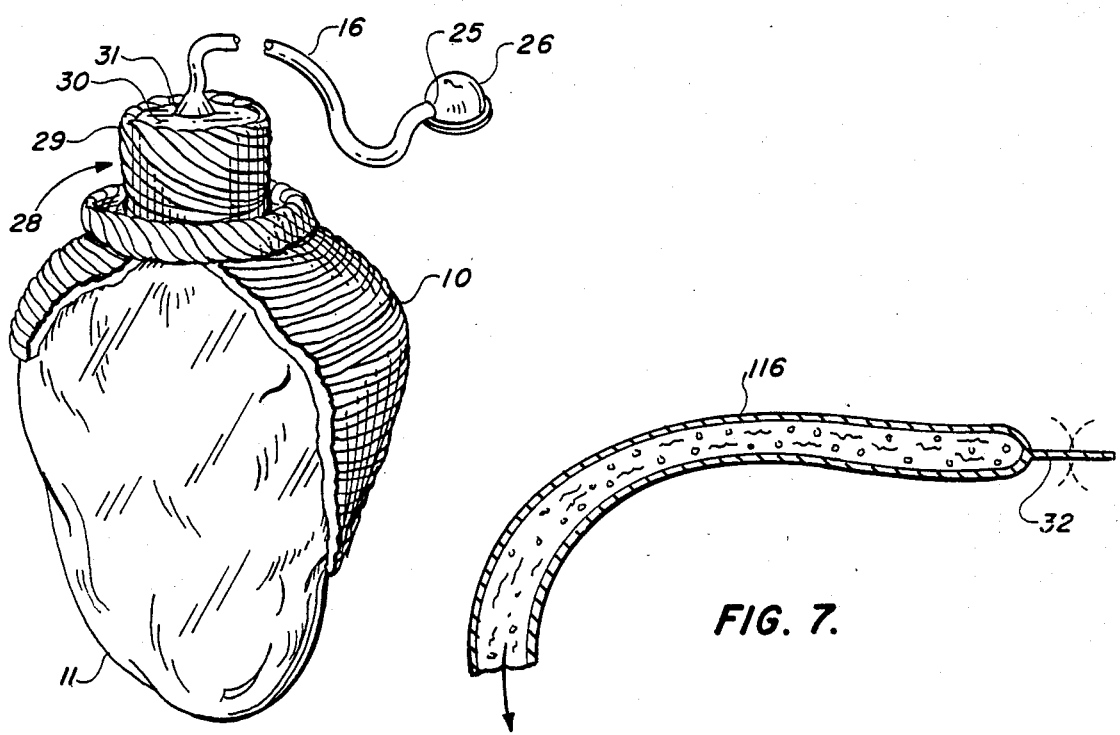
FIG. 6.
FIG. 7.
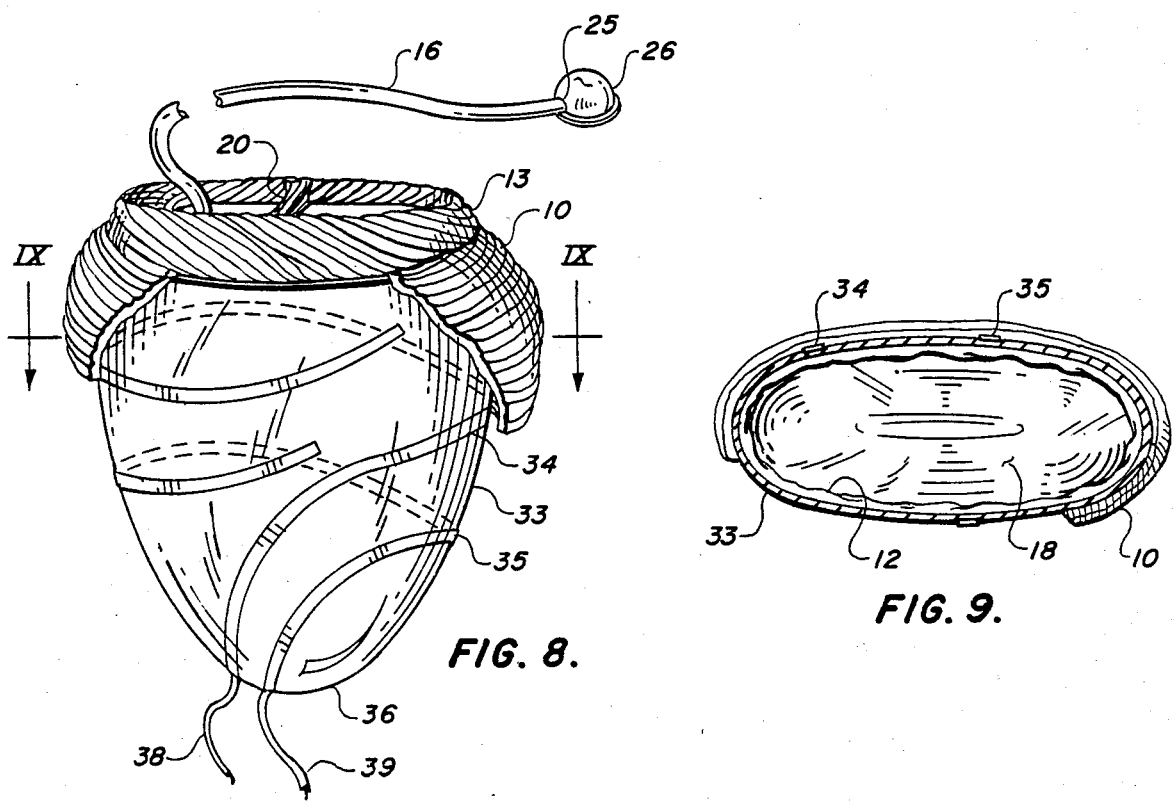
FIG. 8.
FIG. 9.

AUTOGENEOUS PUMPING CHAMBER AND PROCEDURES THEREFOR

INTRODUCTION

The present invention relates generally to the management of degenerative heart disease and more particularly to means and methods of creating an autogenous pumping chamber for ventricular replacement or an assist pumping mechanism thereby avoiding heart transplantation, or artificial pumping devices.

BACKGROUND OF THE INVENTION

Heretofore ventricular failure of the human heart gave rise to severe measures such as the interconnection of the patient to a mechanical heart such as the so-called "Jarvik Heart" which has been the object of much recent press; the transplantation of a human heart into the patient which can be accomplished only when a healthy donor organ is available; or ad libitum muscle patching.

In spite of the widespread notoriety each of these approaches has received, none have demonstrated the ability to substantially prolong life except when measured against the zero expectation believed to confront the patient at the time the procedure is performed.

In fact, the mechanical heart appears at best to be a temporary measure, has a high incidence of thrombus formation, and has serious size limitations while human heart transplants are severly limited by donor availability, tissue incompatibility and rejection phenomanae which create serious post-operative problems and, frequently, death. In addition, the prior procedures are extremely expensive and, in the case of those dependent on the government or private sector insurance, are gradually becoming cost prohibitive.

Accordingly, a need truly exists for the provision of new means and methods of effecting heart ventricle replacement assist or temporary bypass which is not limited by the availability of healthy donor organs, can avoid the rejection phenomena and associated problems, avoid thrombus formation and substantially reduces hospital and physician costs. It is toward the solution of that need that the present invention is directed.

SUMMARY OF THE INVENTION

The present invention comprises an autogenous pumping chamber for ventricular replacement or ventricular assistance wherein the patient's own muscle is used in coaction with a pouch or implant formed of silicone or like pharmacologically acceptable materials to create a body which can thereafter be trained to be paced, that is, rhythmically contract. The autogeneous pumping chamber is then capable of acting as a heart ventricle or mechanical assist without incurring the trauma of heart transplantation. The autogeneous body created hereby results from the body's response to an implant disposed within the patient's own muscle mass which proceeds to form a capsule or pumping chamber, in addition to creating a chamber, therewithin, forms a simulated lining which limits clot formation on the wall of the pumping chamber and thereby avoids the perilous consequences of uncontrollable formation of thrombi thereupon.

The novel implant, autogenous pumping chamber and techniques of the present invention successfully avoid the severe problems heretofore arising and potentially dire consequences resulting therefrom when no donor heart is available for transplantation, or when a transplant is available but is rejected, or when an undue incidence of thrombi occur during and post transplant. Furthermore, practice of the present invention will significantly reduce the extensive costs of hospital, physician and post operative care.

The procedure of the present invention to create a autogeneous pumping chamber which can serve as a ventricular simulating body is multistaged and involves first placing the pharmacologically compatible implant within the rectus (abdominis) muscle or other large striated muscle mass; wrapping the muscle mass, e.g. the rectus muscle, around the implant to completely cover the implant; sewing the rectus muscle upon itself to achieve a closed system; attaching a nerve stimulating system to train the muscle to act as a cardiac muscle; filling the wrapped implant or pouch through its fill system with sterile saline solution; monitoring the filled pouch; adding additional sterile saline solution through the fill system into the pouch by percutaneous injection at weekly intervals for a period of two to six weeks or until pouch obtains a volume approximately two times its initial volume; monitoring the expanded pouch for adverse events for an additional one to two months, draining the saline from the fully expanded pouch; removing the implanted pouch from within the formed muscular shell or pumping chamber; attaching a pacemaker to the main nerve supply which has been skeletonized; and, while maintaining the heart on temporary by-pass, attaching the pumping chamber to the appropriate atrium and outflow vessel (i.e., aorta or pulmonary artery) in the patient's cardiovascular system when it is desired to replace a diseased ventricle, or to another main vascular inflow and outflow when an assist pumping chamber is desired.

Accordingly, it is a principal object of the present invention to provide an autogeneous pumping chamber for ventricular replacement as an efficacious and cost effective alternative to organ transplantation.

Another object of the present invention is to provide a new and improved ventricular simulating autogeneous pumping chamber which overcomes rejection phenomena and substantially eliminates the formation of mural thrombi.

A still further object is to provide a unique two-stage procedure for installing a ventricle simulating autogeneous pumping chamber which requires minimal surgical time and avoids rejection, thereby limiting both the duration of the hospital stay and the ultimate cost.

Still another object is to provide a technique for creating and installing in a needy host an autogeneously generated pumping chamber formed of striated muscle and which has been trained to contract rhythmically over a prolonged time to simulate a healthy heart.

Yet another object of the present invention is to provide a novel procedure for inducing the formation of an autogeneous pumping chamber which can be employed either as a ventricular replacement or as an assist pumping chamber in the treatment of cardiovascular disease.

These and still further objects as shall hereinafter appear are readily fulfilled by the present invention in a remarkably unexpected manner as will be readily discerned from the following detailed description of an exemplary embodiment thereof especially when read in conjunction with the accompanying drawing in which like parts bear like numerals throughout the several views.

BRIEF DESCRIPTION OF DRAWINGS

FIG. 6 is a perspective showing of an alternative embodiment of the present invention;

FIG. 7 is a fragmented cross-section of an alternate fill tube employed in one practice of the present invention;

FIG. 8 is a perspective showing, partially broken away, of an alternative implant of the present invention; and FIG. 9 is a cut-away cross-sectional view taken on line IX—IX of FIG. 8 after an autogeneous pumping chamber has been formed thereupon.

DESCRIPTION OF PREFERRED EMBODIMENTS

The present invention will be described in detail with reference to a preferred embodiment thereof, that is, the creation and installation of an autogeneous pumping chamber for ventricular replacement or ventricular assistance. The autogeneous pumping chamber, as it is herein called, is created from the patient's own muscle. The autogeneous chamber created in accordance herewith, can thereafter be paced to rhythmically contract and thus function as a heart ventricle replacement or as a pumping assist mechanism. The coaction of the silicone implant with the formation of scar tissue by the muscle creates a pumping chamber having an inner lining which is quite smooth so as to limit and substantially preclude the formation of clots on the wall thereof, a major factor in the overall consideration of the procedure.

Figure 3:
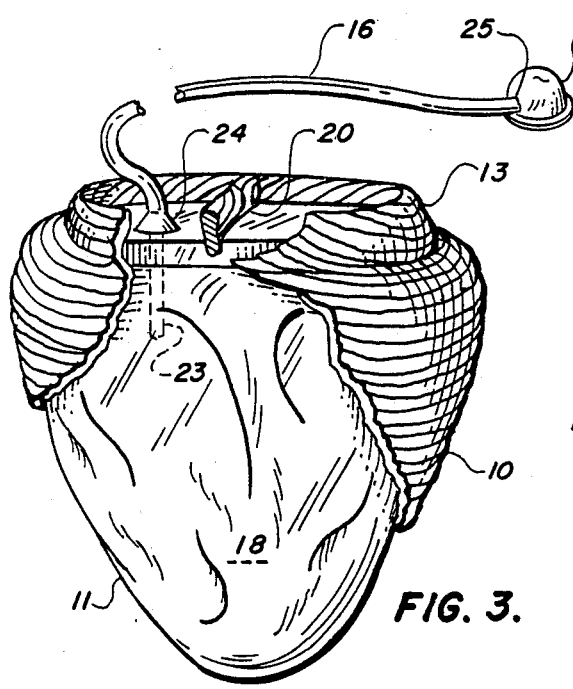
FIG. 3 is a front view of the autogeneous pumping chamber of FIG. 1 showing the fill tube in place.
Figure 4:
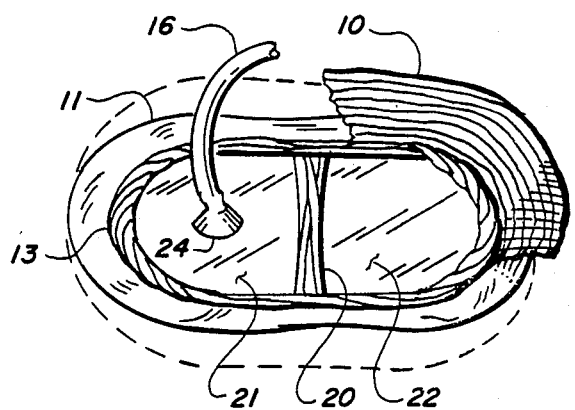
FIG. 4 is a top view of the autogeneous pumping chamber of FIG. 3 showing its expansion in phantom.
Figure 5:
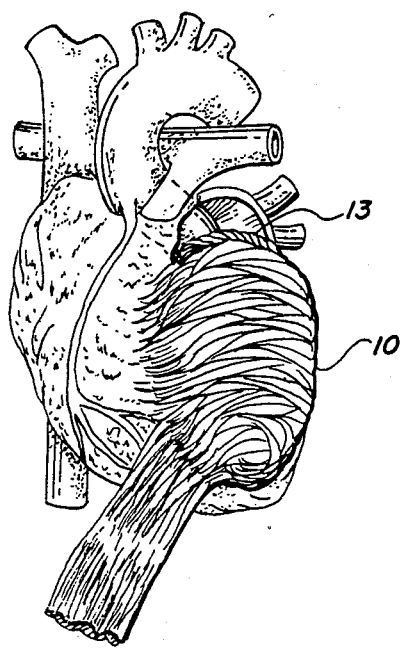
FIG. 5 is a cut-away view of a typical human heart having an autogeneous pumping chamber operatively connected thereto in accordance with the present invention.

Referring now to the drawing, in which FIG. 1-4 illustrate one embodiment of the present invention and FIG. 5 illustrates a human heart having the implant-induced autogeneous pumping chamber operatively associated therewith, the use of the implant to create the muscular chamber pursuant hereto and the surgical procedures required to place the autogeneous chamber in operative relationship to the human cardiovascular system will now be described.

Figure 2:
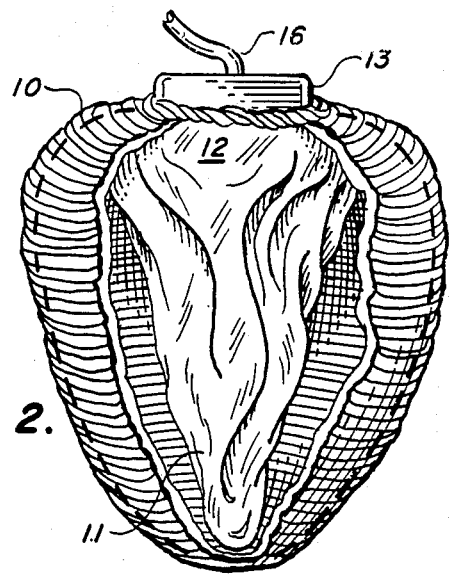
FIG. 2 is a side view of the autogeneous pumping chamber of FIG. 1 showing its expansion in phantom.

The autogeneous pumping chamber embodying the present invention is herein identified by the general numeral 10. Chamber 10 is created around an implant or pouch 11 which preferably is formed of silicone sheeting or like non-toxic suitable material. Pouch 11, as shown in FIGS. 2 and 3, comprises a generally almond shaped body portion 12 which converges to a neck 13 which in turn is connected to and enclosed by suture tab formed of rigid silicone or other pharmacologically acceptable silastic or plastic material. A fill port 15 is constructed in and defined by suture tab to receive and retain a fill tube 16, the function of which will be hereafter described in detail.

Body portion 12 and suture tab coact to define an enclosed chamber 18 therewithin having, in the usual case, a height of about 8-10 cm and a transverse dimension of about 12 cm. At rest, chamber 18 has a volume of 100-150 cc and it expands to about 200 cc for a male adult. The capacity of chamber 18 will be provided with slightly less capacity for female adults and children.

Figure 1:
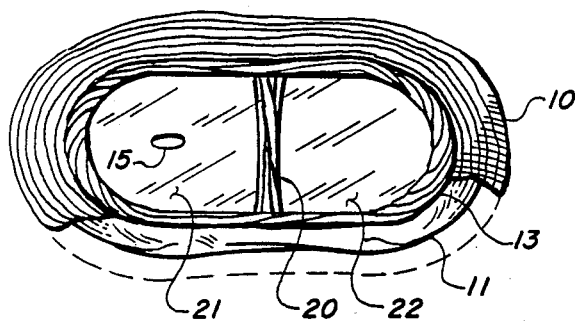
FIG. 1 is a top view of an autogeneous pumping chamber and implant embodying the present invention.

Referring to FIGS. 1 and 4, neck 13 has an internal length of about 10 cm and an internal width of about 4 cm. A centrally convergent groove 20 essentially divides the neck area into a first compartment 21 and a second compartment 22, each of which has a depth of from about 1.0 cm to about 1.5 cm.

Fill tube 16, as shown in FIG. 3, comprises a first end portion 23 extending downwardly through fill into port 15 communication with chamber 18, and it is covered by an appropriate domed cover 24. At the distal end 25 of fill tube 16 a second domed fitting 26 is mounted into which, as will appear, saline solution is injected to fill chamber 18.

In one practice of the present invention, the abdomen of the host is opened with a midline incision and the rectus muscle or like major muscle or muscle group is located. The rectus muscle will be made visible by using a right paramedian or a low transverse incision to elevate the overlying skin and fat. A fascia is opened in the muscle just below the umbilicus and it is raised until the neuro-vascular bundle coming off of the superior epigastric artery is located. The rectus muscle is wrapped around the pouch 11 perferably twice, to completely cover the implant with muscle and the muscle is then stitched to itself to create a closed system.

The rectus fascia will be sutured around the elevated neck 13 of the implant with the fill tube 16 disposed in a subcutaneous pocket and sutured in a triangular fashion for ease of palpitation.

Once emplaced, the pouch 11 is filled with bacteriostatic isotonic saline to provide volume (see dotted line in FIG. 2) and the muscle permitted over time to develop a scar at the interface with the silastic implant. When the autogeneous chamber 10 is fully formed, the volume of the pouch is reduced by withdrawing the saline fluid through the fill tube 16 having placed an incision just above the neck, the neck having been wrapped with the muscle fascia. The silastic pouch is then withdrawn from the muscle chamber through the fill port 15 leaving an integral chamber of muscle which has grown together to create a fluid-tight entity herein designated autogeneous pumping chamber 10.

The exact relocation of this muscular pouch is determined by the function it will be called upon to perform by the surgeon. Thus as an assist, it will be disposed in the abdomen while as a replacement, it will be disposed adjacent the heart and connected by grafts or tubes. Suitable grafts include cadaver, human autografts and acceptable synthetic vascular graft material such as, GORTEX and the like.

To install the autogeneous chamber 10 at the heart, the chest cavity is opened and chamber 10 is rotated to the heart while leaving it connected to the superior epigastric artery in the manner of an Island Pedicle Flap. Then, the neck is sutured to an appropriate inflow/outflow such as the left atrium and the aorta as shown in FIG. 5. Once secured, a pacemaker is attached to the main nerve of the muscle with a conductive probe to pulse the atrium in the conventional fashion.

In one precise practice of the surgical procedure employed in the present invention, the abdominal exposure will be created from the pubis to the costal margin. The anterior rectus fascia will be opened in its midline. The inferior edge of the rectus muscle will be incised and elevated from the posterior fascia. The muscle will be raised approximately ⅔rds around the implant 11 in a spiral fashion. After two complete thicknesses of the muscle have been wrapped about the pouch 11, three to four vertical openings in the superior edge of the muscle will be made and three to four strips or flaps of the interior portion of the muscle will be made to place through the openings and sutured on the muscle to maintain the wrapping in place. The incisions will be closed after the integrity of the expanding prosthesis is checked, that is, when the unimpeded flow of injectable saline through the fill dome 24 into the body portion 12 of pouch 18 is visually verified.

The implant 18 will be filled at the time of surgery with between 50 to 150 mls. of saline, depending upon the patient's size (child, female, adult male, etc.). Over a period of four to six weeks at weekly intervals, additional sterile saline solution will be added by percutaneous injection through fill dome 24 and fill tube 16 while the muscle is trained. By "training the muscle", as that term is used herein, I refer to the electrical connection of a nerve stimulator (Neuromod ®, Medrionic) to the main nerve of the muscle to cause the muscle to quiver and prepare it to respond later with rhythmic contraction and expansion when a pacemaker is associated therewith in a similar fashion, that is, with an electrically conductive probe.

When body portion 12 of implant 11 achieves a filled volume of approximately two times its initial volume, the entire assemblage is left in place within the body of an additional one to two months.

Thereafter, a second operation is performed during which the implant 11 is removed from within the autogeneous pumping chamber, the nerve stimulator is removed by withdrawing the connective probe from the main nerve of the muscle, and a pacemaker is connected into the main nerve supply entering superiorly into the muscle chamber 10 which has been skeletonized. While maintaining the patient on bypass, the newly constructed autogeneous pumping chamber, if to be used for ventricular replacement, is attached to the left atrium and aorta of the patient for which it assumes the function of the diseased ventricle or provides an assist pumping chamber.

From the foregoing it can be seen that a method of forming an autogeneous pumping chamber for use as a replacement ventricle or ventricle assist has been described which can be paced to rhythmically contract and expand like an original heart ventricle or heart.

The procedure can be characterized as comprising three parts, namely: the first surgery; the in vivo muscular chamber formation and muscle training; and the second surgery.

The first surgical procedure comprises placing implant 10 (herein called the "Gibney Ventricular Stimulating Implant" or "GVSI") within a rectus (adominis) muscle and wrapping the muscle around the implant, sewing the muscle upon itself to achieve a closed system; and filling the interior of body portion 12 of implant 11, after wrapping with muscle, via fill tube 16 through fill port 15.

Thereafter, the in vivo formation of the autogeneous pumping chamber is achieved by adding additional fluid (sterile isotonic saline) into the body portion 12 by percutaneous injection through fill tube 16 and fill port 15 over a period of four to six weeks at weekly intervals; and maintaining the rectus wrapped implant in vivo for one to two months during which time the nerve stimulation is perfected and the muscle merges into an integral chamber.

Thereafter, the second surgical procedure is performed which comprises removing the implant 11, and fill tube 16 from within the pumping chamber 10, inserting a pacemaker into the main nerve supply, and substituting the resulting autogeneous pumping chamber 10 for the deceased ventricle or connecting it as an assist while sustaining the patient on a conventional bypass during the procedure.

While the rectus muscle has been herein indentified as used in the practice of the present invention, other major muscle and muscle groups such as the Latissimus Dorsi, the Pectoralis Major, the Quadricep and the Diaphragm are also prime candidates for the procedure hereof.

Furthermore, when the device hereof is to be used as an auxiliary pumping station, pumping chamber 10 and implant 11 may use a silicone fill tube 116 having a self-sealing silicone gum disposed therein and attached by a tab 32 (see FIG. 7) at the distal end thereof to an adjacent surface.

In grafting chamber 10, conventional or Y-grafts, formed of a suitable silicone material or GORTEX ® and the like may be employed.

Referring now to FIG. 6, an alternative embodiment of the present invention is shown which is especially adapted for use as a cardiac assist which includes a closed member 28 formed upon suture tab and extending upwardly therefrom about 2–3 cm. Closed member 28 comprises a cylindrical body portion 29 enclosed at its upper end with circular portion 30 into which an alternate fill port 31 is formed for receiving fill tube 16 therewithin in the manner previously described. The saline solution can be introduced into fill tube 16 by injection into fill dome 24 (see FIG. 6) or by inserting an appropriate needle directly into the self sealing fill tube 116 (see FIG. 7).

A further embodiment of the present invention is shown in FIGS. 8 and 9 and is especially adapted for use when prior nerve damage or other exigencies do not allow a conventional pacemaker hook up to the main nerve of the muscle selected to create chamber 10. Specifically this embodiment involves a muscular pumping chamber 10 formed about a pouch 11 in exactly the same general manner as is described above. However in this practice, pouch 11 is first wrapped in a polyurethane shell 33 having a thickness of about 1 to 2 mil and having a pair of non-corrosive electrically conductive strips or wires 34, 35 disposed therein starting adjacent the bottom 36 thereof and coiling up about body portion 12 in spaced relationship to each other toward the top thereof. During the development of the autogeneous chamber 10, the muscle literally grows into the polyurethane and conductive wires 34, 35 are scarred in place on the inner wall of muscle chamber 10 and remain so positioned when pouch 11 is subsequently removed through fill port 15 in accordance with the earlier description. When this chamber 10 is placed with use, the pacemaker will be connected to conductors 34, 35 at the exposed ends 38, 39, thereof, respectively.

From the foregoing, it is apparent that means and methods have been herein described and illustrated which fulfill all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

Accordingly, what is claimed is:

1. The method of producing an autogeneous pumping chamber having a preselected volume within a host comprising the steps of opening the abdomen of a host and locating therein a major muscle or muscle group selected from the group consisting of rectus abdominus, latissimus dorsi, pectoralis major, the quadricep, and the diaphragm; wrapping said muscle or said muscle group about a pouch-shaped implant formed of a pharmacologically acceptable plastic and having body portion and a fill port defined therein in communication with the interior of said body portion; partially filling said interior of said body portion with isotonic saline; thereafter periodically injecting additional isotonic saline into said interior of said body portion until said preselected volume is obtained; waiting for an additional period of time while said body portion is filled to its preselected volume until said muscle or muscle group forms an integral liquid-tight scar chamber thereabout; withdrawing said saline from within said implant; and withdrawing said pouch-shaped implant from within said scar chamber.

2. The method of claim 1 wherein a nerve stimulator is attached to a main nerve of said wrapped muscle to train said muscle to react like a cardiac muscle in response to a pacemaker operatively connected thereto.

3. The method of claim 1 in which said major muscle is the rectus muscle.

4. The method of claim 2 in which said major muscle is the rectus muscle.

5. The method of claim 1 in which said pouch-shaped implant is first wrapped in a polyurethane shell having first and second electrically conductive means disposed therewithin and coiled thereabout in spaced relationship to each other.

6. The method of claim 5 in which said polyurethane shell is permanently embedded into the inner wall of said autogeneous pumping chamber.

7. An autogenous pumping chamber for ventricular replacement or assist in a host having a cardiovascular system comprising a fluid-tight muscular chamber having a smooth wall lining therein formed of specifically transformed major muscle or muscle group selected from the group consisting of rectus abdominus, latissimus dorsi, pectoralis major, the quadricep, and the diaphragm, said muscle or muscle group having a main nerve, said chamber being operatively connectable into the cardiovascular system of said host, and said main nerve of said muscle or muscle group being connectable to a pacemaker.

8. An autogeneous pumping chamber for ventricle replacement or assist in a human host comprising a body portion formed of a specifically transformed major muscle or muscle group selected from the group consisting of rectus abdominus, latissimus dorsi, pectoralis major, the quadricep, and the diaphragm and having a chamber defined therewithin, said chamber having a smooth wall lining formed therein by said transformed muscle or muscle group, said smooth wall lining further being liquid tight an inflow connectable to the left atrium or pulmonary vein, and an outflow connectable to the aorta of said host; said chamber being pretrained to respond to the application of a pacemaker thereto.

9. An autogeneous pumping chamber according to claim 8 in which said chamber has a pair of conductors embedded therein in spaced coiled relationship to each other for connecting said pacemaker thereto.

10. An autogeneous pumping chamber according to claim 8 in which said major muscle or muscle group has a main nerve coacting therewith and said pacemaker is connected thereto.

* * * * *